United States Patent [19]
Lau et al.

[11] Patent Number: 4,921,644
[45] Date of Patent: May 1, 1990

[54] MUCIN DIRECTED LIPSOME

[75] Inventors: John R. Lau; W. Blair Geho, both of Wooster, Ohio

[73] Assignee: Technology Unlimited, Inc., Wooster, Ohio

[21] Appl. No.: 162,275

[22] Filed: Feb. 29, 1988

[51] Int. Cl.$^5$ .................... A61J 5/00; B32B 5/16; A01N 25/00

[52] U.S. Cl. .................... 264/4.1; 428/402.2; 428/402.24; 424/450; 604/890.1

[58] Field of Search .................. 424/450, 417, 461; 252/316, 356; 264/4.1, 4.3, 4.6; 428/402.2; 514/78.2, 26; 536/5

[56] References Cited

U.S. PATENT DOCUMENTS

| | | | |
|---|---|---|---|
| 4,145,410 | 3/1979 | Sears | 424/450 |
| 4,501,728 | 2/1985 | Geho et al. | 424/450 |
| 4,614,796 | 9/1986 | Kawamata et al. | 536/5 |
| 4,751,219 | 6/1988 | Kempen | 514/26 |
| 4,762,720 | 8/1988 | Jizomoto | 424/450 |
| 4,762,915 | 8/1988 | Kung et al. | 530/405 |
| 4,765,987 | 8/1988 | Bonte et al. | 424/450 |

Primary Examiner—Barry S. Richman
Assistant Examiner—T. J. Wallin

[57] ABSTRACT

Mucin coated Sepharose is used as a laboratory model to measure the affinity of a postulated lipid composition in liposome configuration for binding to mucin. The preferred lipid composition provides a first lipid moiety which projects a postive charged ion. A second lipid moiety enhances the positive charge by neutralizing all intermediate negative charges of the first lipid. The result is a liposome with strong postive charge areas which will bind to mucin.

4 Claims, 3 Drawing Sheets

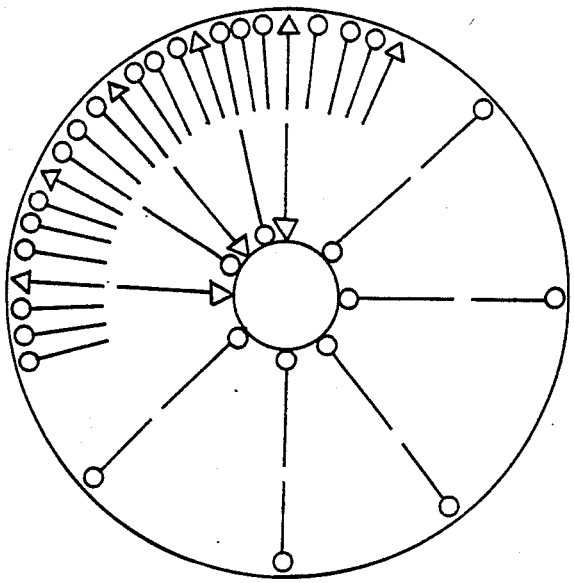
FIG. 1
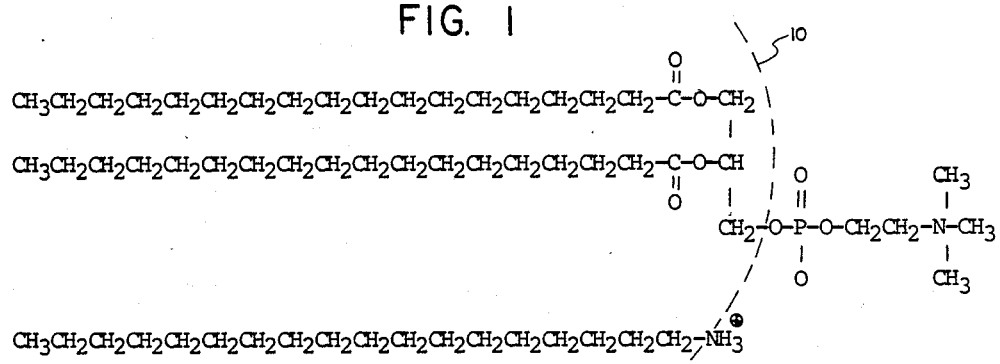
FIG. 2
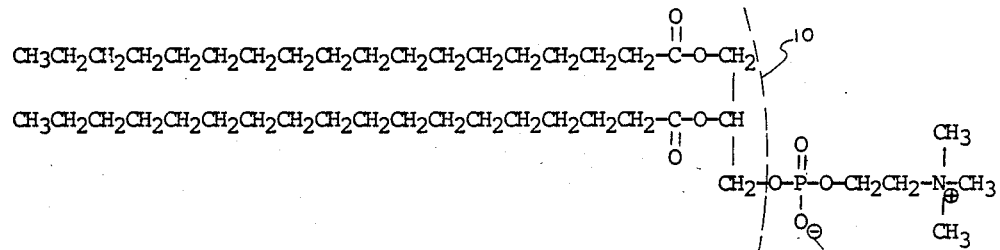
FIG. 3
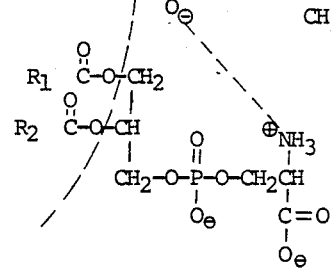

MUCIN DIRECTED LIPSOME

BACKGROUND OF THE INVENTION

1. Field of the Invention

Targeted vesicle/liposomes.

2. Description of Prior Art

The exact name to apply a lipid bladders is an open question. Generally, a vescile is smaller than a liposome, and unilamellar, whereas a liposome is multilamellar. Liposome is a term which wil be used hereafter because it embraces more forms of lipid bladders. This writing will assume a general knowledge of the state of the art of the preparation of liposomes, incorporation of drugs, proteins, and genetic material therein, and targeting. A through presentation of these aspects of liposomes is set forth in a three volume compilation of writings by acknowledged authorities, edited by Gregory Gregoriadis, published by CRC Press, Inc., 2000 Corporate Boulevard, N.W., Boca Raton, Fla., U.S.A., entitled *Liposome Technology*.

A liposome is generally illustrated by a circular array of symbols representing hydrophilic head groups with lipophilic long chain tail groups. See FIG. 1. It is understood that a liposome is a bladder, roughly spherical in form and subject to distortion to a considerable degree without rupture. It is formed from a mixture of lipids forced into a bladder form by an application of energy, such as by sonication or microfluidic procedures.

The surface generated by the hydrophilic head groups of liposomes has not been of particular concern to prior art development, other than to enclose a core volume space. The surface relationship of the lipid components is all-important in this invention.

The prior art has sufficiently developed the need and use of cholesterol and other ingredients in liposome structure to provide fluidity and charge-charge repulsion to prevent coagulation. The ingredients of a typical prior art liposome, however, may be listed as follows:

A. Preferred bulk bipolar lipid constituents (75-95%) selected from:
  1. Distearoyl lecithin (DSL)
  2. Dipalmitoyl lecithin (DPL)
  3. Other lecithins with chain lengths C10-C20.

B. Minor constituents (0.1-25%) for stability selected from:
  1. Cholesterol

2. Dicetyl Phosphate

Liposome technology has advanced the delivery of drugs, diagnostic materials, and cosmetics by capturing the substance of interest in the core volume or wall of the liposome, and using one of the following techniques:

(1) injecting a quantiy of the liposomes into the blood system of a warm blooded host and allowing the substance to escape slowly as the vesicles age and disintegrate. .

(2) including an incomplete lipid in the liposome wall, which will cause the wall to leak the core volume contents. The rate of leaking is controllable by varying the amount of the inclusion.

(3) attaching a molecule having an affinity for the target entity, which entity takes in the liposome and utilizes the core volume substance, or, in the case of cosmetics, the targed liposome is held in place on the target while leaking the cosmetic (i.e. breath freshener, etc.). This latter procedure is the subject matter of the copending U.S. Ser. No. 877,862, now U.S. No. 4,767,615 wherein the hydroxyapatite of teeth serves as the anchor target.

There is no known targeting molecule, or other means of binding a liposome to mucin tissue, prior to the present invention.

SUMMARY OF THE INVENTION

No target molecule is known to exist for targeting a liposome to mucin in a warm-blooded host.

This invention provides a combination of lipid materials in a liposome, some of which have hydrophilic head groups composed of a tandemly positioned, mean, negative charged moiety, an extreme positioned positive charged moiety, and some of which terminates in a positive charged head moiety extending to a position substantially adjacent said mean moiety, whereby the negative charge of the mean positioned moiety is neutralized by the other lipid rather than by the extreme moiety, resulting in a lipid membrane wall exhibiting local areas bearing a net positive charge. The positive charged liposome has been demonstrated to be strongly attracted to mucin.

DEFINITION

Polar lipids when placed in a water environment form lipid bilayers, and when sonicated, will form liposomes (vesicles) with the lipid chains clustered in the interior of the membrane and the hydrophilic head groups extended into the water environment.

The distance any head group extends into the water environment will be a function of its structural formation.

In this description of the preferred embodiment of the invention, that portion of the hydrophilic head adjacent the junction with the lipid moiety, which is essentially the point of origin of the head, and be termed the "proximal" position. Another terminology is the mathematical term "mean" position.

"Proximal" is a more widely known term and will be the preferred expression hereinafter.

That portion of the head moiety away from the point of attachment, known as the "distal" moiety, may also be referred to as the extreme position. Again, the term "distal" is preferred.

BRIEF DESCRIPTION OF THE DRAWINGS

For a fuller understanding of the nature and objects of the invention, reference should be had to the following detailed description taken in connection with the accompanying drawings in which:

FIG. 1 is a commonly used means to illustrate the structure of a liposome formed of bi-polar lipids.

FIGS. 2-5 are illustrations of the spatial relationship of two lipid components of a liposome wall structure used to study and test this invention.

Similar reference characters refer to similar parts throughout the several views of the drawings.

DETAILED DISCUSSION

Figure 4:
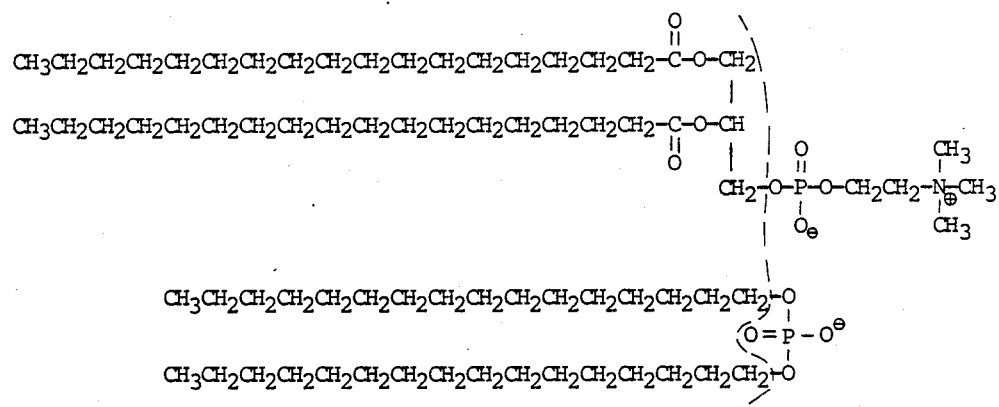
Figure 5:
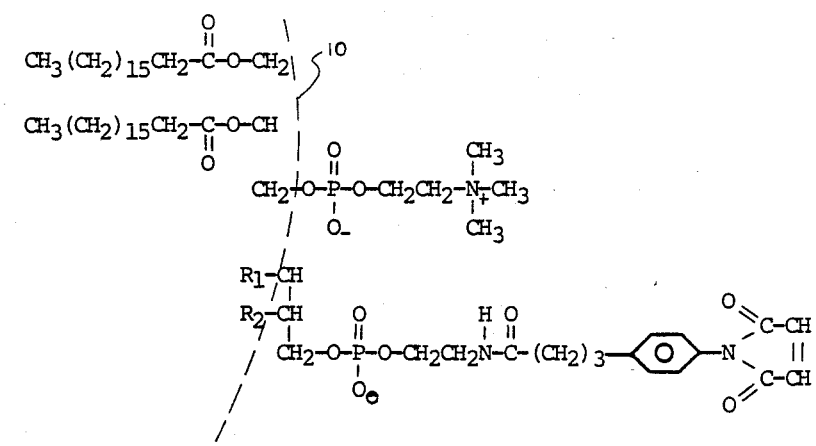

In order to seek out the maximum benefit from among several possible operational embodiments, five models were proposed and tested in vitro. Then, five models were proposed and sent to an independent laboratory to test in vivo.

The in vitro test:

An example of tissues in man and other animals that have mucin as one of the primary constituents includes the eye, ear, nose, throat, esophagus, stomach, intestinal tract, bladder, urinary tract, and vagina.

Mucin is a microprotein and consists of voth polysaccharides and protein. Submaxillary mucin is a protein polysaccharide of approximately 800 disaccharides or sugar units, each of which is N-acetyl neuraminyl (2-6) N-acetyl glactosamine attached to a single polypeptide chain. The carbohydrate of sugar accounts for approximately 45% of the molecular weight, whereas the protein accounts for the remaining 65%. The disaccharide or sugar units and the protein are bound to each other via glycosidic linkage from the C-1 hydroxyl group of the amino sugar moiety to the -hydroxyl groups of serine and threonine residing on this protein. The carbohydrate or sugar is attached to about every 6th or 8th residue of the peptide chain. The overall negative charge to mucin is contributed by the negatively charged carboxyl group on the N-acetylneuraminyl moiety. The structural formula is set forth below: The above structure and description are taken from White, Handler and Smith *Biochemistry*, 5th edition, page 988.

The inventive concept to be set forth herein is that a liposome, when composed of charge-balancing polar lipids, will enhance and accentuate the positive head groups of those lipids which project positively charged moieties spaced away from their lipophilic "R" groups. Furthermore, the accentuated positively charged head groups will project beyond the area where the charge-balancing of the polar lipids occurs.

The procedure employed in this in vitro study was to provide a slurry of cyanogen bromide activated Sepharose to which the mucopolysaccharide mucin could be bound. Sepharose, Agarose, and Sephadex are trade names of bead-formed gel of dextran and epichlorohydrin. These products are well known for their use in chromatographic procedures and may be purchased from Pharmacia Biotechnology, Uppsala, Sweden.

The purpose of the cyanogen bromide activated Sepharose beads for this study for the invention is to provide a mucin model to determine the best compositions for later in vivo testing as reported hereinafter.

The glycoprotein, bovine submaxillary mucin was linked to the cyanogen bromide activated. Sepharose (agarose) in order to establish a binding matrix for vescile attachment. This mucin-Sepharose then serves as a laboratory model of mucin tissue to enable accurate binding tests of the lipid liposomes of this invention.

Five test samples, numbered as set forth in Table 1 below, were prepared by well known liposome procedures. Basically, the indicated lipids of each sample were solubilized in organic solvent, vacuum dried, suspended with an appropriate buffer, and sonicated. Each sample included a like portion of $^{14}C$ cholesterol label. The label was employed for study evaluation and will not be present in medical procedures.

TABLE I

| Sample Code | (Symbol reference below Table.) | | |
|---|---|---|---|
| | DSL | | CHOL |
| #743 | | DCP | |
| mg | 49.8 | 9.83 | 3.48 |
| u moles | 62.96 | 18.00 | 8.99 |
| mole ratio | 7 | 2 | 1 |
| #744 | | | |
| mg | 64.10 | 0 | 3.48 |
| u moles | 81.03 | 0 | 8.99 |
| mole ratio | 9 | | 1 |
| #745 | | SA | |
| mg | 49.8 | 4.85 | 3.48 |
| u moles | 62.96 | 17.99 | 8.99 |
| mole ratio | 7 | 2 | 1 |
| #746 | | MPB-PE | |
| mg | 47.8 | 17.68 | 3.48 |
| u moles | 62.96 | 18.00 | 8.99 |
| mole ratio | 7 | 2 | 1 |
| #747 | | Spoiled preparation. | |
| #748 | | PS | |
| mg | 49.7 | 13.8 | 3.48 |
| u moles | 62.96 | 18.85 | 8.99 |

PS - Phosphatidyl serine
DSL - Distearoyl Lecithin
DCP - Dicetyl Phosphate
CHOL - Cholesterol
SA - Stearylamine
MPB-PE - p-maleimide phenyl butyrate phosphatidyl ethanolamine The above compositions were chosen on the basis of the postulate that the correct spatial or three-dimensional orientation of the functional target molecule will produce maximum and specific binding. The inventive concept to be tested is that the main offset distance between the functional end groups of the liposomal membrane surface plays a key role in targetability and functionality of the liposomal delivery system.

Charged liposomes are developed (used), wherein a positive charge is contributed by a primary amino function to bind to the mucin substrate. It is not known why this preferred embodiment is efficacious. Presumably, it is possible because mucin may have a negative charge, and opposite charges attract. However, other explanations are also possible, such as the proposal that hydrogen bonding can hold a liposome to the mucin. This would be accomplished by the liposome donating hydrogen atoms from the primary amine to the carbonyl functions on the proteinaceous portion of the mucin molecule. In addition to hydrogen bonding, salt bridges provide another means of creating electrostatic attractions between the vescile surface and the mucin substrate. What is known, is that establishing areas of concentrated positive charge, results in excellent mucin binding. That discovery is the basis for the claimed invention.

Refer to FIG. 1 of the drawings. The small circles represent the hydrophilic moiety of the lipid. Because the lipids are placed in a water environment, the lipid tail or "R" groups project toward one another, thus producing a bipolar film, which, upon sonication, produces a bipolar liposome bladder wall. The bladder "wall" is simply the resultant of packing the hydrophilic head groups in close juxtaposition.

If only one lipid were employed, the head end groups would define a fairly smooth surface. The smoothness of the surface is relative. At the submicroscopic level there will actually be an undulating but uniform configuration. All known polar lipids capable of forming a bipolar liposome have head groups which exhibit balanced negative and positive charges.

See FIG. 2. DSL has two long carbon chains which terminate in a glycerol backbone just at the film surface, with a phosphate group and quaternary ammonium ion moiety, the latter extending outwardly as defined by a choline function. The phosphate group is negatively charged, and the quaternary ammonion ion is positively charged at physiological pH. They substantially neutralize each other, resulting in a neutral surface.

The discovery of this invention points to the fact that the mean distance between the functional end groups and the vesicle membrane surface plays the key role in targetability and overall functionality of the vesicle delivery system. Neutralization of the phosphate group by a positive end group of another lipid, DSL will then exhibit a positive charge because its phosphate is no longer a neutralizing influence.

This discovery is punctuated by the fact that several lipid compositions were evaluated in vivo and in vitro testing, and the preferred embodiment elicited a marked positive response. Other compositions have a lesser response and were determined to be below the level of the preferred embodiment.

The foregoing general overview will be more fully understood by the following specific structural formulas and the resultant in vitro tests.

In Vitro Preliminary Study

The illustrations in FIGS. 2-5 depict the three-dimensional orientation of the target molecules as they protrude from the vesicle membrane surface.

FIG. 2 illustrates a structural formula for distearoyl lecithin (DSL). The dotted line 10 represents what may be said to be the primary membrane surface, and the phosphate group lies at that surface. Distearoyl lecithin terminates in a choline moiety which presents a quaternary ammonium moiety spaced about 14 Å from the primary surface 10. The phosphate group will lie on, or possibly 2 Å units out of the general primary surface 10 and bears a net negative charge. The tandem charges of the distearoyl lecithin are so closely spaced that they effectively neutralize each other through charge-charge interaction. This is the normal relationship configuration of most liposome uses.

Normally it is efficacious to have a substantially neutral surface charge, or, if any charge is available, it is employed for charge-charge repulsion to prevent coagulation and has no usefulness in targeting.

This invention is based on the discovery and concepts explained best with reference to FIG. 2 of the drawing. In FIG. 2, the fragment of a liposome primary surface, shown by line 10, is essentially composed of distearoyl lecithin and stearylamine. The experimental proof of the invention has employed a ratio of 7 moles of distearoyl lecithin to 2 moles of stearylamine. This basic ratio can be increased to a 1:1 relationship, but actual experimention has found that 7:2 is very effective.

The reason for the effectiveness of the spatial relationship of charged moieties, as shown in FIG. 2, is that the stearylamine has an ammonium hydrophilic head moiety. Because of this closeness to the surface 10, the ammonium head moiety is closer to the phosphate group of the distearoyl lecithin than the distance of the phosphate group from the quaternary ammonium ion group of the lecithin moiety. Accordingly, the positive charge of the ammonium head of the stearylamine produces a neutralizing effect upon the phosphate group of the lecithin. The result is that the strong positive charge on the choline head group of the lecithin moiety is now the dominant charge of the liposome surface at that position. Because of the preferred ratio of 7:2, the described positive influence will be moderately distributed but sufficient. The importance of this positive charge in targeting to mucin of the living body will be fully developed hereinafter.

In order to establish the viability of the invention, a first in vitro experiment was conducted. In this experimental work $^{14}C$ cholesterol and the appropriate lecithins were incorporated into the lipid liposome membranes for radiochemical tracing purposes. These liposome preparations were evaluated for their binding affinity toward the glycoprotein, bovine submaxillary mucin.

Liposomes prepared as described supra, were incubated with mucin-activated Sepharose at ambient temperature for 15 minutes in 10 mM $KH_2PO_4$—$K_2HPO_4$ buffer pH 7.4.

Each vesicle preparation was evaluated in its ability to bind mucin-Sepharose as well as reagent grade Sepharose. Reagent grade Sepharose was used as a control for each experiment since no vesicle binding was expected with this matrix, and the test proved the prediction.

Figure 6:
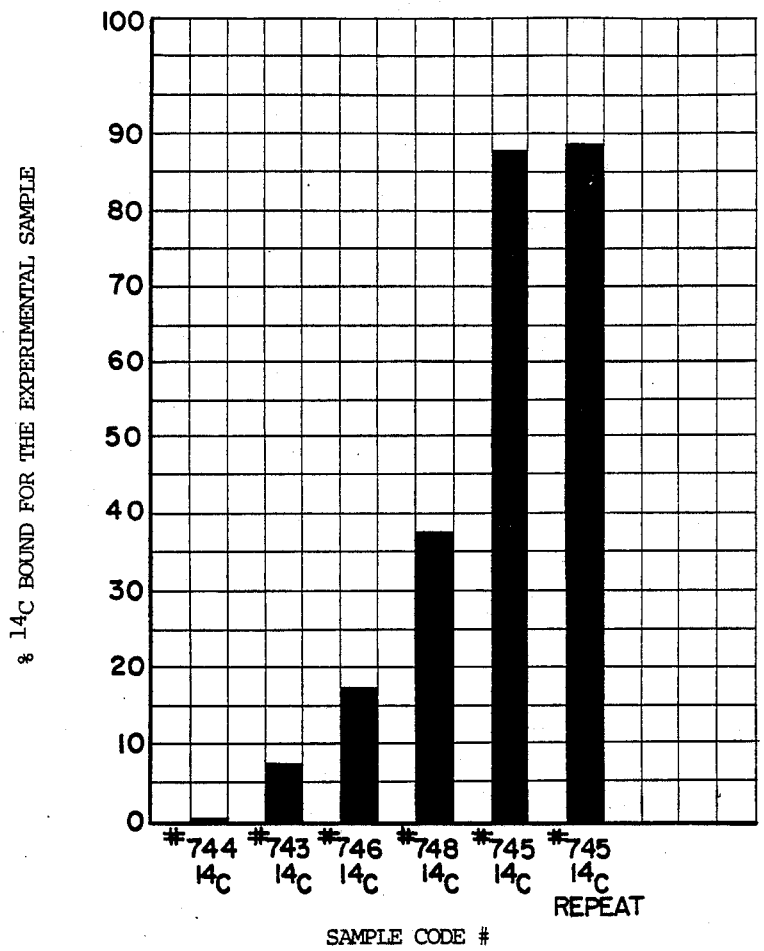
FIG. 6 is a bar graph of the percentage of "$14_C$" labelled vesicles bound to a Sepharose-mucin matrix.

The graph in FIG. 6 illustrates the percentage of $^{14}C$ cholesterol labelled vesicles bound to the Sepharose-mucin matrix for each of six separate evaluations. The liposomes were incubated with a contant amount of the Sepharose-mucin matrix in a conical centrifuge tube. After a set period of time the tube constituents were centrifuged in order to pellet the matrix. The supernatant was then sampled and compared to the control sample. Vesicle binding was determined by difference between the control supernatant and the vesicle-Sepharose mucin supernatant.

First, compare experiments 744 and 745. The experimental group 744 is made of distearoyl lecithin as the main ingredient and was exposed to a column of mucin-Sepharose to determine the ability of the lecithin (DSL) to adhere to mucin. In group 744 of the table of FIG. 6, it will be seen that essentialy no measurable amount of the DSL-structured liposomes is retained.

The liposomes of FIG. 2 were then prepared wherein there was a 7:2 mole ratio of DSL to stearylamine. According to the concepts of this invention, it was postulated that the ammonium head group of the stearylamine would neutralize the negative phosphate charge on the DSL and accentuate the strong positive charge of the quaternary ammonium ion. If a resultant positive charge is achieved, it would then cause the vesicle to adhere to the mucin-Sepharose. The results shown in the Table of FIG. 6 bear out the postulation by the exceptionally strong adherence of the sample 745 to the mucin-Sephadex column. Because of the extraordinary results of the first experiment, the 745 experiment was repeated with substantially identical results as shown in the FIG. 6.

In order to test the viability of the experiment described with respect to sample 744 and 745, it was postulated that a terminal end group projecting a positive charge farther from the defined surface of the liposome, but not as far as the terminal quaternary ammonium ion of the DSL, would function to neutralize the action of the DSL phosphate group but would be less effective than the stearylamine, but more effective than the straight DSL.

Refer to FIG. 3. With the phosphatidyl serine of FIG. 3, the $NH_3$ positive charge only partially neutralizes the phosphate charge of the DSL because of the greater space relationship. This experiment was labelled sample 748 in Table 1, and the result of retention is shown in the graph of FIG. 6. The retention was less than half as effective as the experiment of sample 745. This bears out the postulation that the charge on the phosphate group was less effectively neutralized, thus resulting in a lesser positive surface charge then obtained in sample 745. However, the use of less than ultimate accentuation of the choline positive charge is useful and within the scope of the invention.

Continuing the proof experiments even further, sample 743 was prepared using dicetyl phosphate (DCP) as shown in FIG. 4, and Table 1. DCP presents a phosphate group substantially identical to the phosphate group of DSL without the quaternary ammonium ion terminal group. Thus, the DCP was essentially not effective in enhancing the positive charge of the DSL. However, some aberration in the experiment did cause about 7% of the vesicles to be retained by the column. See FIG. 6.

The final experiment was done with sample 746 which employed p-maleimide phenyl butyrate phosphatidyl ethanolamine. See FIG. 5. This trial produced the results shown in the graph of FIG. 6. Very little accentuation of the positive charge was observed. Accordingly, in vitro experimental work summarized in the table of FIG. 6 established a foundation for anticipation of actual in vivo testing.

The foregoing description has indicated the presence only of radio tagged members which may be employed for test purposes only. No medication of any kind has been referred to.

It is well-known in the art to load liposomes in a core volume with water soluble medications or topical applications such as perfume, skin ointments, and a variety of moisturizing members. The hydrophilic water soluble materials are usually released by means of incorporating lyso-lecithin as one of the liposome composition members in order to create a pore which causes the liposome to be referred to as a "leaky" liposome.

This invention is not directed toward the application of any particular medication to the mucin tissues. Selection of medication and incorporating into liposomes is old and well-known in the prior art.

This invention is in the method of composing a liposome characterized by an enclosing lipid wall with the desired cargo. The lipid wall, made according to this invention, has affinity for mucin membranes of a warm blooded host. There are a number of ways of producing liposomes, the oldest of which is sonication, and a later development employs microfluidization. Whether by either of these methods or another perhaps yet undiscovered method, the advance provided by this invention is to employ a mixture of lipids, a first one of which has an acyl moiety which will anchor into the wall of the liposome because it is lipophilic. The selected first lipid also has a choline moiety which always bears a positive charge. Finally, the selected liposome has an interconnecting phosphatidyl moiety interconnecting the choline and the acyl moieties.

Normally, such a lipid has a resultant neutral influence on the wall of the liposome because the phosphatidyl moiety is negatively charged and therefore neutralizes the capability of the choline to exert a positive charge.

According to this invention, a second lipid is employed which has a hydrophilic head moiety which bears a positive charge and is incorporated preferably at a lower mole ratio than the choline headed lipid, but may be employed in a full one-to-one ratio in some instances. The purpose of having the second lipid less than the first is in order to neutralize only parts of the first lipid and thereby create a spotty positive charge around the surface of the liposome.

If a full one-to-one ratio of the first and second lipids are not employed, then the balance of the mixture should include at least some cholesterol in order to produce a more fluid liposome.

The result is a bipolar lipid molecule having a first type molecule with the hydrophilic head group in tandem, the tandem grouping having a negative charged moiety in a mean position and a positive charged moiety in an extreme position. These tandem relationships result in a substantially neutral effective charge. Then, a second type molecule with a positive charge hydrophilic head moiety extending less than the extended position of the tandem molecule positive charge is effective to neutralize the mean position moiety of the first type molecule allowing the extreme tandem moiety to exhibit a positive charge to the environment. The reason that the positive spotty charges will cause mucin binding has not been determined, but the effect of the balanced inclusion of lipids has been shown conclusively to be highly effective and of great utility.

POSTULATION FROM IN VITRO TEST

If a liposome is produced with strong positive charge surface areas, then the whole composition of matter should be expected to bind to mucin.

IN VIVO CONFIRMATION—LIPOSOME RETENTION

Having shown in vitro that the choline head moiety of distearoyl lecithin (DSL) will provide an effective positively charged liposome surface if the phosphatidyl phosphate subgroup is neutralized, five more compositions were made as set forth in Table 1, and given numbers 816–820. For reference, the sample numbers correspond as set forth below:

743–817
744–816
745–820
746–818
748–819

The above 800 series samples were prepared and sent to an independent laboratory in Ft. Worth, Tex. in order to evaluate the results in vivo. Although not listed in the contents of Table 1 above, each of the samples contained a $^{14}C$ cholesterol label for testing purposes. The $^{14}C$ cholesterol would not be employed in actual human medication, and is employed in these experiments only for the purpose of determining a confirmation of the postulated results.

Rabbits were used as the test animals for this in vivo analysis. Each tranquilized rabbit was dosed with 10 microliters of preparation in each eye. Within five minutes after dosing, the rabbit was sacrificed and samples removed in about 30 minutes. Each preparation was tested in three rabbits resulting in six eyes per preparation. The samples were placed in vials and at a later time processed for liquid scintillation counting. The best retention was obtained with the positively charged liposome of sample 820 which corresponds exactly with the results obtained in the sample 745 in vitro testing. In this preparation about 46% of the radioactivity label dosed on the eye was recovered. Most of the radioactivity was retained in the nictating membrane and the eyelid conjunctiva. The best corneal retention was also achieved with positively charged liposomes of sample 820. With the sclera, the percent recoveries of the radioactive label were relatively low considering that the sclera samples were of greater weight and surface area than the corneal samples.

The mucin coated sphadex technique did indeed correctly predict that the stearylamine liposomes would have the greatest retention.

Figure 7:
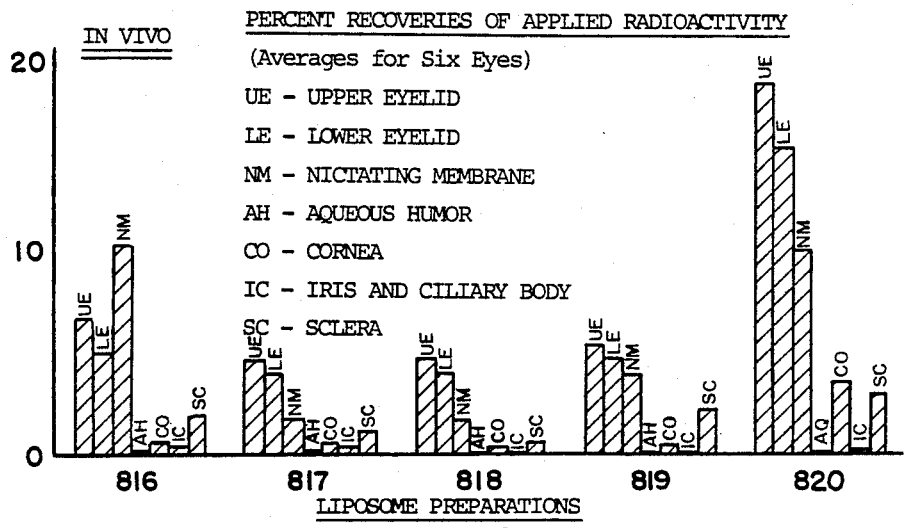
FIG. 7 is a graph of recovered radioactivity from tissue used in Vivo experiments.

For a visual comparison, the results of recovery of applied radioactivity is shown in FIG. 7.

The entire experiment was completed within 2 hours after sacrificing the rabbits. After removal, the tissues were stored in a balanced salt solution enriched with bicarbonate, dextrose and glutathione. The entire cornea was removed along with a strip of eyelid conjunctiva and sclera. The tissue samples were removed from the storage solution and spread flat on a glass slide. A measured volume of liposome preparation was applied with a Hamilton syringe. After a minute, the tissue was rinsed by tilting the glass slide and vigorously rinsing the top of the tissue with about 3-4 ml of the balanced salt solution.

The radioactivity recovered from the rinsed tissues is shown in FIG. 7 and the correlation between the in vitro experiments set forth in FIG. 6 above is clearly shown. Those liposomes which were caused to have a positive charge exhibited on the surface thereof adhered to the mucin tissues far above the neutral surface liposomes containing only distearoyl lecithin. For a full comparison of results, the FIGS. 6 and 7, being the in vitro and in vivo experiments respectively, should be compared.

What is claimed is:

1. A liposome having a wall structure comprising:
   first and second amphipathic lipid molecules,
   said first lipid molecule having a hydrophilic headgroup and lipophilic hydrocarbon tails,
   said head group of the first lipid molecule having a negative charge moiety proximate to said tails and a positive charge moiety distal to said tails,
   said negative and positive charged moieties together resulting in a substantially neutral effective charge with respect to the head group, and,
   said second lipid molecule having only a positive charged hydrophilic head moiety, and lipohilic hydrocarbon tails,
   said second molecule positive charged head moiety extending substantially adjacent to the position of the negative charge moiety of the first lipid and neutralizing the negative charge moiety of said first lipid molecule, whereby the said distal moiety of said first molecule is free to exhibit its positive charge to the environment and will bind to mucin.

2. An article of manufacture comprising:
   a first component which is a pharmaceutical agent, said first component being carried by a second component which comprises lipid membrane structures in the form of liposomes;
   said membrane structures being composed of first and second polar lipid molecules;
   said first polar lipid molecules having a substantially neutral resultant and charge effected by a distal functional group bearing a positive charge and a proximal functional group interconnecting said distal group to a lipid tail group;
   said proximal functional interconnecting group having a negative charge;
   said negative and positive charged functional groups together resulting in a substantially neutral effective charge with respect to the environment;
   and said second polar lipid molecules having only a positive charged functional group interconnected to a lipid tail group and extending substantially adjacent to the position of the negative charged moiety of said first lipid molecule;
   whereby the positive group of said second molecules and the interconnecting negative charge group of the said first molecules neutralize one another, leaving the said distal functional positive group of said first molecules dominant and the liposomes will therefore bind to mucin.

3. A liposome as defined in claim 2 wherein the first lipid molecule is distearoyl lecithin and the second lipid molecule is stearylamine.

4. The method of composing a liposome characterized by an enclosing lipid wall having affinity for mucin membranes of a warm blooded host, comprising the steps of:
   providing a first lipid having an acyl moiety, a choline moiety bearing a positive charge, and an interconnecting phosphatidyl moiety bearing a negative charge;
   providing a second lipid having a hydrophilic head moiety bearing a positive charge extending substantially adjacent to the position of the negative charge moiety of the first lipid; and,
   energizing a mix of said first and second lipids to liposome form,
   whereby the said mixture of lipids produces a net positive charge which will bind to mucin and anchor the liposome.

* * * * *